United States Patent [19]

Kawanabe et al.

[11] Patent Number: 5,488,854
[45] Date of Patent: Feb. 6, 1996

[54] PIPETTING APPARATUS

[75] Inventors: Junichi Kawanabe; Masaaki Takeda; Hitomi Katagi; Yuko Kato, all of Mitaka, Japan; Brent A. Pelletier, Mundelein, Ill.

[73] Assignee: Abbott Laboratories, Abbott Park, Ill.

[21] Appl. No.: 295,691

[22] PCT Filed: Dec. 22, 1992

[86] PCT No.: PCT/JP92/01681

§ 371 Date: Oct. 17, 1994

§ 102(e) Date: Oct. 17, 1994

[87] PCT Pub. No.: WO93/18409

PCT Pub. Date: Sep. 16, 1993

[30] Foreign Application Priority Data

Mar. 3, 1992 [JP] Japan .................... 4-045171

[51] Int. Cl.$^6$ .................................................. G01N 7/00
[52] U.S. Cl. ............................................................ 73/19.05
[58] Field of Search ................................ 73/864.11, 19.1, 73/19.05; 340/626; 422/100

[56] References Cited

U.S. PATENT DOCUMENTS

| | | | |
|---|---|---|---|
| 4,117,727 | 10/1978 | Friswell et al. | 73/864.21 |
| 5,054,650 | 10/1991 | Price . | |
| 5,059,171 | 10/1991 | Bridge et al. . | |
| 5,182,938 | 2/1993 | Merkel | 73/19.05 |

Primary Examiner—R. Raevis
Attorney, Agent, or Firm—Mark C. Bach

[57] ABSTRACT

The presence of air bubbles is detected during a dispensing of samples for determining if the volume of the sample dispensed is insufficient.

The characteristic of a presence-of-bubbles curve (101) has a difference in a pressure inside a nozzle from the characteristic of a curve (100) under a normal condition in which no bubbles exist, at the time just before the dispensing of the sample is completed. Accordingly, it is possible to determine whether or not bubbles exist by detecting the pressure inside the nozzle at the determination time (105) and comparing the detected value with an established threshold value, and it is determined that an insufficient volume of sample has been dispensed, thereby a warning is generated.

3 Claims, 2 Drawing Sheets

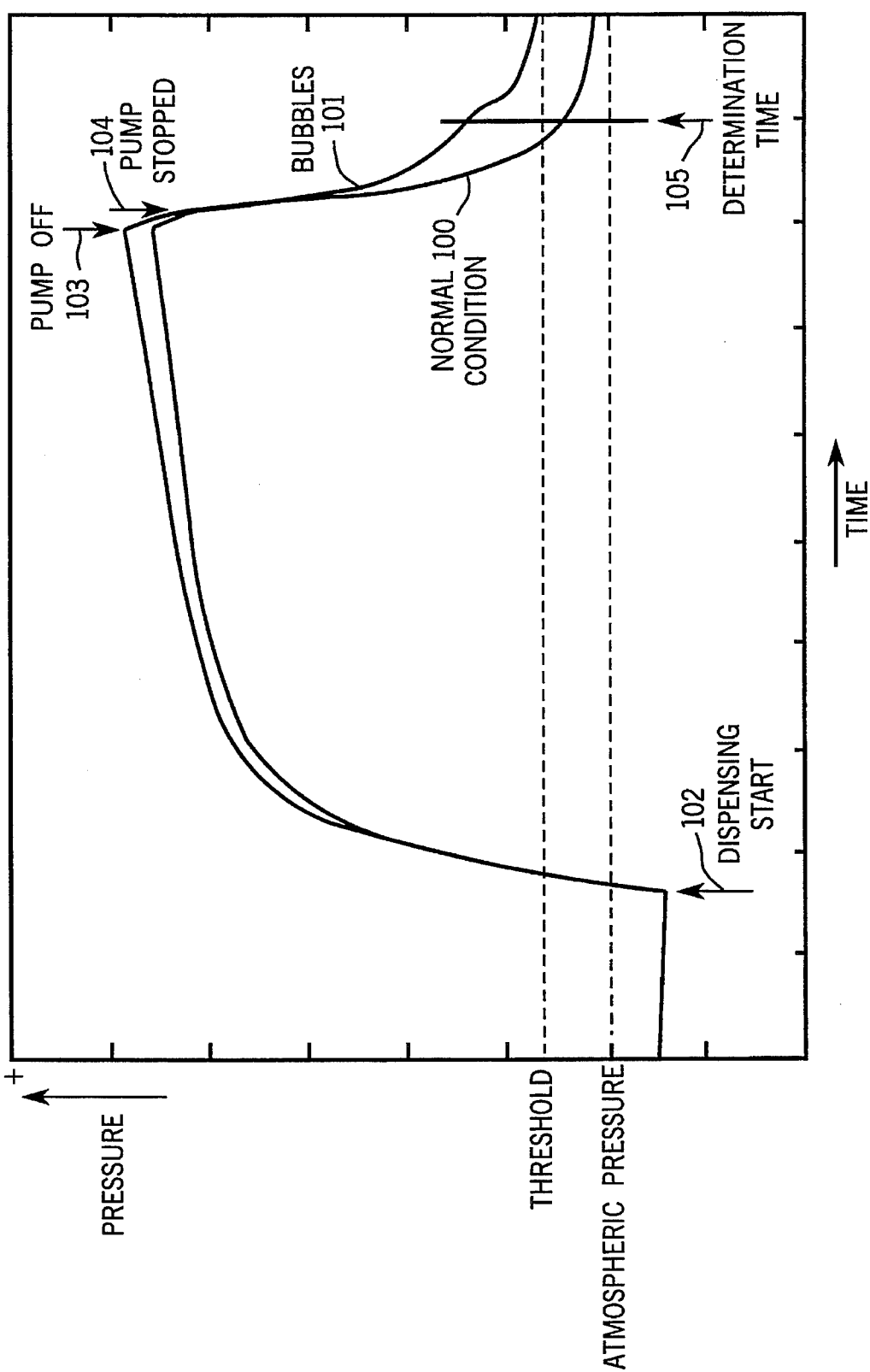

PIPETTING APPARATUS

REFERENCE TO RELATED APPLICATIONS

This application is the U.S. national phase of patent application Ser. No. PCT/JP92/01681 filed on Dec. 22, 1992 and is the U.S. equivalent of Japanese patent application No. 45171/92 filed on Mar. 3, 1992 and still pending.

DETAILED DESCRIPTION OF THE INVENTION

1. Field of Industrial Utilization

The present invention relates to a pipetting apparatus, and more particularly relates to a pipetting apparatus having the ability to determine if the volume of a sample dispensed is insufficient, during the dispensing of samples into containers with the use of a nozzle, by detecting the presence of air bubbles inside the nozzle, for instance.

2. Description of the Prior Art

There are known pipetting apparatuses for pipetting samples, which are used, for example, as distribution apparatuses that distribute blood extracted from human bodies and the like into a plurality of containers.

In such apparatuses, aspiration of the sample is performed through a disposable nozzle. In this case, in order to make certain that a prescribed volume of sample is pipetted, it is required to make sure that an appropriate volume of sample is aspirated into the inside of the nozzle at the aspirating operation. However, when such aspiration is taken place without considering presence of bubbles, the accuracy of the volume of sample aspirated will not be precise if bubbles get aspirated together with the sample. Consequently, the volume of such sample pipetted will have a lower degree of accuracy.

In this connection, the applicant of this application previously proposed in Japanese Laid-Open Publication No. 2-196963, a pipetting apparatus, in which the pressure within an air tube connected to the nozzle is detected by a pressure sensor when aspirating sample, whereby an insufficient aspiration of the sample is determined when an integrated value of the detected pressure is lower than a predetermined reference value.

The Problem to be Solved by the Invention

However, if the volume of sample being dispensed is not precise at the time when the sample is dispensed, it is not possible to improve the pipetting accuracy. Namely, when tiny bubbles like foams seen in beer are generated due to vibrations and the like caused when the nozzle is being moved, and then thus generated tiny bubbles float up to collect near the top part of the sample contained in the nozzle, there is a case that these bubbles remain in the inside of the tip of the nozzle even after the sample has been dispensed, resulting in an inaccurate volume of sample being dispensed. Moreover, after a sample has been dispensed, there is a case that a small amount of the sample remains in the form of a balloon-shaped bubble that is formed around the tip of the nozzle and dangles down therefrom, and this also results in an inaccurate volume of sample being dispensed. Of course, in the conventional apparatus, factors such as the adhesion of the sample on the inside walls of the nozzle have been taken into account when determining the volume of sample to be aspirated. However, the above-mentioned unexpected cases have not been taken into their accounts.

Moreover, in the apparatus disclosed in Japanese Laid-Open Publication No. 2-196963, since the method for detecting an insufficient volume of sample is carried out only at the time of aspirating the sample, it is not possible for the apparatus to detect an insufficient volume of sample dispensed as a result of some volume of the sample remaining behind at the time of dispensing. Furthermore, as bubbles may momentarily go undetected during the aspiration of a sample, this further emphasizes the need for a way of detecting the presence of bubbles at the time of dispensing of a sample in order to improve the accuracy of the volume of sample pipetted.

The present Invention has been made in view of the above-mentioned problems. Therefore, it is an object of the present invention to provide a pipetting apparatus which can detect presence of bubbles inside the nozzle or in the vicinity of the tip thereof just before the dispensing of the sample is completed.

Means for Solving the Problem

In order to achieve the above-mentioned object, the present invention is directed to a pipetting apparatus which includes a nozzle for carrying out aspirating and dispensing of a sample, a threshold value memory which stores a prescribed threshold value, a pressure sensor for detecting the pressure inside the nozzle at a prescribed determination time just before the dispensing of a sample has been completed, and a determination section that determines the presence of bubbles when the actual pressure inside the nozzle which is detected by the pressure sensor exceeds the threshold value.

Operation

According to the above construction, at the prescribed determination time the pressure sensor directly or indirectly detects the pressure inside the nozzle, and then this detected value is compared with the threshold value stored in the threshold value memory. At this time, if the detected value exceeds the threshold value, the determination section determines that bubbles are present.

Namely, at the moment when the dispensing of a sample has been completed, if some portion of the sample in the forms of tiny bubbles remain inside the tip of the nozzle or when a balloon-shaped bubble is formed around the tip of the nozzle, or if tiny bubbles are discharged out of the nozzle Just before the completion of the dispensing of the sample, such bubbles become obstructions that block the opening of the tip of the nozzle. At this time, the dispensing air supplied from a pump to the inside of the nozzle for dispensing the sample is affected by the resistance of the bubbles that remain behind. As a result, the pressure inside the nozzle remains above the usual pressure. Accordingly, at the moment when this change in pressure arises relative to the usual pressure just before the dispensing of the sample is completed, or more concretely stated, at the moment when most of the sample has been dispensed, by observing the pressure inside the nozzle at any time before the pressure inside the nozzle has returned to the atmospheric pressure, it is possible to determine the existence of bubbles and thereby determine that an insufficient volume of sample has been dispensed.

In this regard, it should be noted that in order to obtain a proper volume of dispensed sample, it is essential for the apparatus to aspirate an accurate volume of sample. For this purpose, it is preferable to combine with the present invention a means for determining whether or not an accurate volume of sample has been aspirated, such as the means disclosed in the above-mentioned Laid-Open Publication No. 2-196963.

DESCRIPTION OF THE PREFERRED EMBODIMENT

Hereinbelow, a preferred embodiment of the present invention will be explained with reference to the drawings.

FIG. 1 illustrates in block diagram form the essential elements of a preferred embodiment of a pipetting apparatus according to the present invention.

As shown in FIG. 1, for the purpose of pipetting a sample, a nozzle 10 is provided to carry out the functions of aspirating and dispensing the sample. In the present embodiment, a disposable type nozzle is utilized for the nozzle 10. The nozzle 10 is in turn held by an XYZ robot that enables the nozzle 10 to be freely movable in any side-to-side or up-and-down direction.

The nozzle 10 is connected to a pump 16 via an air hose 14. The pump 16 is comprised of a cylinder 18 and a piston 20 and serves as a means for generating an aspirating force and a dispensing force. Connected to the air hose 14 is a pressure sensor 22 that detects the pressure inside the air hose 14, thereby enabling detection of the pressure inside the nozzle 10. Pressure detection signals outputted from the pressure sensor 22 are fed to a limiting circuit 26 after being amplified by a DC amp 24. The limiting circuit 26 serves to prevent excessive current from flowing into an A/D converter 28 provided as the next element in the sequence of elements. The A/D converter 28 in turn converts the signals based on detected pressure into digital signals and then the digital signals are fed to a control unit 30.

The control unit 30 is used to control the overall operations of the pipetting apparatus according to the present invention. For example, the control unit 30 is used to control the operations of the pump 16, the XYZ robot 12 and the like. Furthermore, the control unit 30 includes a determination circuit 32 and a memory 34, the functions of which are described below.

FIG. 2 shows a graph of an example of the change in pressure inside the nozzle 10 over time during the dispensing of a sample. In the graph of FIG. 2, the vertical axis represents the pressure detected by the pressure sensor 22, and the horizontal axis represents the progression of time.

As shown in FIG. 2, a curve 100 represents the change in pressure over time for the dispensing of a sample under the normal condition in which no bubbles exist within the nozzle 10. In this case, the dispensing volume is 200 μl. As for the curve 101, it represents the change in pressure over time for the dispensing of a sample in the case where bubbles exist within the nozzle 10. In the particular case represented by the curve 101, bubbles of the volume of 50 μl are existed therein, with all other conditions being the same as those for the normal condition.

As shown in the figures, when the piston 20 shown In FIG. 1 is pushed into the cylinder 18, a dispensing force is generated which causes the pressure inside the nozzle 10 to rise, and this starts the dispensing of the sample contained in the nozzle 10. Before this operation is begun, the pressure inside the nozzle 10 is below that of the atmospheric pressure in order for the sample to be held within the nozzle 10.

After a certain amount of time has elapsed from the moment that the dispensing of the sample was begun, all the sample will be dispensed. At this time, due to the viscosity of the sample, there is a tendency for the actual time required to dispense the sample to be slightly longer than the dispensing operation time of the pump. This is the primary cause for the occurrence of a smooth decrease in pressure after the pump is turned off. In this connection, as shown in FIG. 2, arrow 103 indicates the point in time when the pump is turned off (i.e., the point in time when the speed of the piston begins to slow down), and arrow 104 indicates the point in time when the action of the pump completely stops.

As shown in the graph of FIG. 2, before the pump is turned off, both the normal curve 100 and the presence-of-bubbles curve 101 have substantially the same characteristics. However, after the pump is turned off, namely, at the moment just before the dispensing of the sample is completed, marked differences arise with regards to the characteristics of the curves 100 and 101. In other words, when the dispensing of a sample is close to being completed, the bubbles that exist in the top portion of the sample contained in the nozzle are either gradually dispensed from the nozzle or remain adhered to the inside of the tip of the nozzle, and the presence of such bubbles creates a resistance that has an effect on the pressure of the dispensing air flowing into the nozzle. This accounts for the upwards shift of the presence-of-bubbles curve 101 relative to the normal curve 100 after the pump has been turned off. Furthermore, as shown in FIG. 2, in the case where some bubbles continue to remain behind in the nozzle, or in the case where a balloon-shaped bubble remains adhered to the tip of the nozzle, the pressure inside the nozzle reaches a constant value that is higher than the atmospheric pressure. In other words, the pressure inside the nozzle does not return to the atmospheric pressure. However, in the case when these bubbles ultimately get discharged from the nozzle, the presence-of-bubbles curve 101 would finally begin to approach the dashed line indicating the atmospheric pressure. However, as shown in FIG. 2 which shows the characteristics of the normal curve 100 and the presence-of-bubbles curve 101 during the interval of time before the occurrence of such final discharge of bubbles, there still be a difference therebetween.

Accordingly, by comparing the pressure detected inside the nozzle with the pressure previously measured for the normal case of no bubbles being present, for example, at the determination time 105 indicated in FIG. 2, it is possible to determine whether or not bubbles exist. For the purpose of carrying out such determination, a threshold value is established, as shown in FIG. 2.

As for the determination time 105, it is preferably set at a time when the difference in characteristics of the normal curve 100 and the presence-of-bubbles curve 101 is easily distinguishable during the interval of time after the pump has been turned off and before the pressure inside the nozzle returns to the atmospheric pressure. With regards to the threshold value, it is established in view of such factors as the viscosity of the sample and the like.

Now with regards to the determination circuit 32 shown in FIG. 1, it carries out determination of the presence or absence of bubbles by comparing the value of the pressure detected inside the nozzle, at the determination time just before the completion of the dispensing of the sample, with the threshold value stored in the memory 34. In the case when the determination circuit 32 determines that bubbles are in fact present, this means that there is an insufficient volume of sample dispensed, and therefore the control unit 30 generates a warning that alerts the person operating the pipetting apparatus.

Effects of the Invention

By using the pipetting apparatus according to the present invention described above, it is possible to determine whether or not bubbles are present when carrying out dispensing of a sample with a nozzle. This determination makes it possible to determine whether or not a sufficient volume of sample has been dispensed, and in the case when it is determined that an insufficient volume of sample has been dispensed, this fact can be reported in the form of a warning to the operator of the pipetting apparatus. Thus, the present invention provides a pipetting apparatus that has improved accuracy.

BRIEF DESCRIPTION OF THE DRAWINGS

FIG. 2 is a graph showing the change in pressure inside the nozzle over time when a sample is being dispensed with the pipetting apparatus of the present invention.

EXPLANATION OF THE REFERENCE NUMERALS

Figure 1:
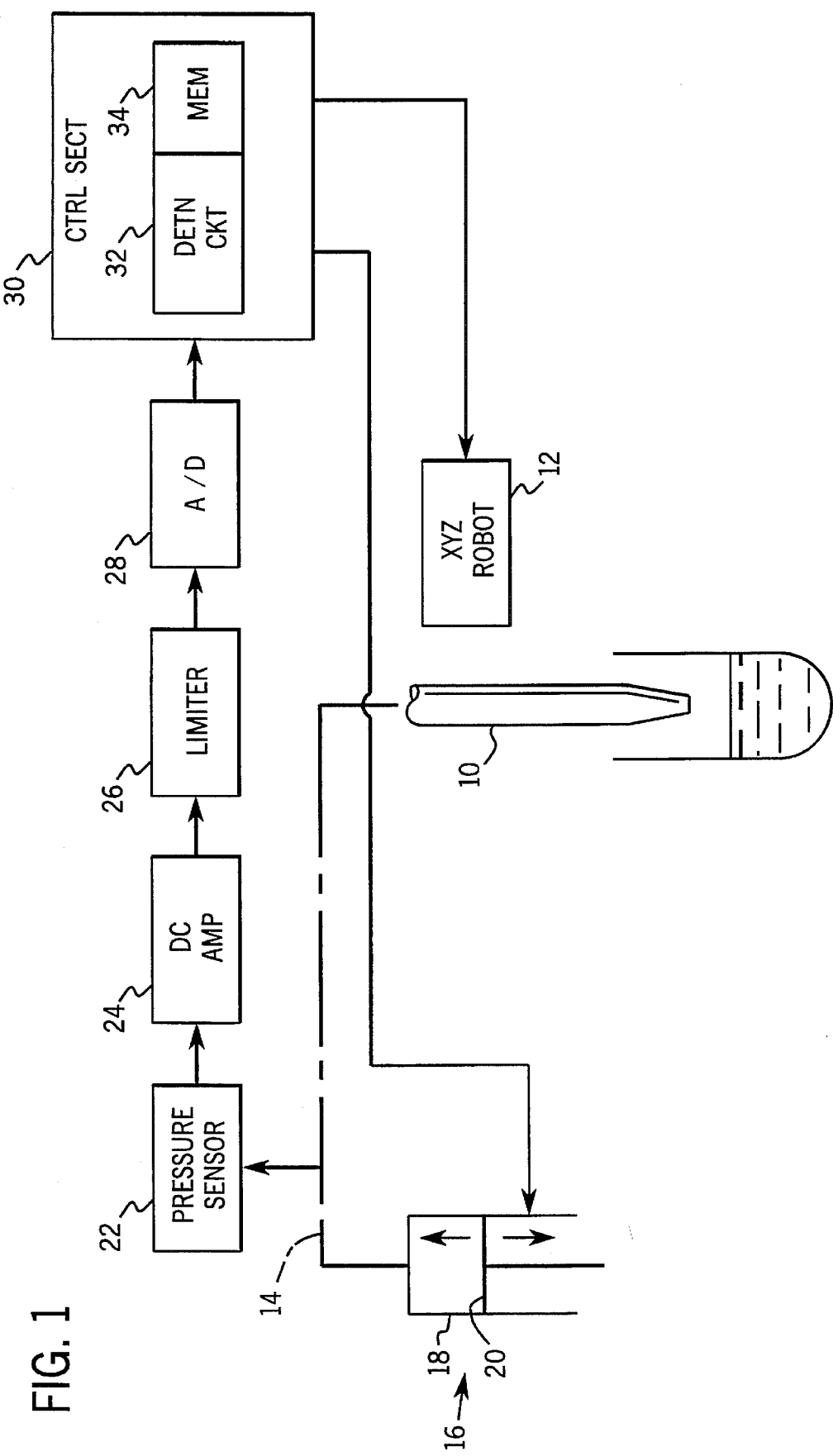
FIG. 1 is a block diagram illustrating the overall construction of a pipetting apparatus according to the present invention.

10 ... Nozzle
16 ... Pump
22 ... Pressure Sensor
30 ... Control Section
32 ... Determination Circuit
34 ... Memory

What is claimed is:

1. A pipetting apparatus having a nozzle for carrying out aspirating and dispensing of a sample, comprising:

(a) a pressure threshold value storage section for storing a prescribed pressure threshold value;

(b) a pressure sensor for detecting pressure inside the nozzle at a prescribed determination time just before completion of the dispensing of the sample; and (c) a determination section which determines presence of bubbles when actual pressure inside the nozzle detected on the basis of output from the pressure sensor exceeds the prescribed pressure threshold value.

2. A pipetting apparatus including a nozzle having a tip portion for aspirating and dispensing a sample, comprising:

(a) a pressure threshold value storage section for storing a prescribed pressure threshold value which is greater than atmospheric pressure;

(b) a pressure sensor for detecting pressure inside the nozzle at a prescribed determination time just before completion of the dispensing of the sample; and (c) a determination section which determines presence of a bubble inside said nozzle Or around said tip portion of said nozzle when pressure inside the nozzle detected by said pressure sensor at the prescribed determination time exceeds the prescribed pressure threshold value.

3. A pipetting apparatus having a nozzle for aspirating and dispensing a sample, comprising:

(a) a pressure threshold value storage section for storing a prescribed pressure threshold value;

(b) a pressure sensor operatively connected with the nozzle for detecting pressure inside the nozzle at a prescribed determination time prior to completion of the dispensing of the sample from the nozzle; and (c) a determination section which determines presence of a bubble Without compressing the sample when the pressure inside the nozzle detected by the pressure sensor exceeds the prescribed pressure threshold value.

* * * * *